United States Patent
Kim et al.

(10) Patent No.: US 10,090,471 B2
(45) Date of Patent: Oct. 2, 2018

(54) DIKETOPYRROLOPYRROLE POLYMER AND ORGANIC ELECTRONIC DEVICE CONTAINING SAME

(71) Applicant: INDUSTRY-ACADEMIC COOPERATION FOUNDATION GYEONGSANG NATIONAL UNIVERSITY, Gyeongsangnam-do (KR)

(72) Inventors: Yun-Hi Kim, Gyeongsangnam-do (KR); Soon-Ki Kwon, Gyeongsangnam-do (KR)

(73) Assignee: Industry-Academic Cooperation Foundation Gyeongsang National University, Gyeongsangnam-do (KR)

( * ) Notice: Subject to any disclaimer, the term of this patent is extended or adjusted under 35 U.S.C. 154(b) by 184 days.

(21) Appl. No.: 14/889,822

(22) PCT Filed: May 30, 2013

(86) PCT No.: PCT/KR2013/004764
§ 371 (c)(1),
(2) Date: Jan. 19, 2016

(87) PCT Pub. No.: WO2014/181910
PCT Pub. Date: Nov. 13, 2014

(65) Prior Publication Data
US 2016/0118588 A1  Apr. 28, 2016

(30) Foreign Application Priority Data
May 7, 2013 (KR) ........................ 10-2013-0051471

(51) Int. Cl.
| C08G 61/12 | (2006.01) |
| C07D 487/04 | (2006.01) |
| H01L 51/00 | (2006.01) |
| C07D 519/00 | (2006.01) |
| H01L 51/05 | (2006.01) |

(52) U.S. Cl.
CPC ........ H01L 51/0036 (2013.01); C07D 487/04 (2013.01); C07D 519/00 (2013.01); C08G 61/123 (2013.01); C08G 61/124 (2013.01); C08G 61/126 (2013.01); H01L 51/0043 (2013.01); C08G 2261/124 (2013.01); C08G 2261/1412 (2013.01); C08G 2261/18 (2013.01); C08G 2261/3223 (2013.01); C08G 2261/3225 (2013.01); C08G 2261/3241 (2013.01); C08G 2261/334 (2013.01); C08G 2261/3327 (2013.01); C08G 2261/344 (2013.01); C08G 2261/414 (2013.01); C08G 2261/592 (2013.01); C08G 2261/92 (2013.01); H01L 51/0053 (2013.01); H01L 51/0545 (2013.01); H01L 51/0558 (2013.01)

(58) Field of Classification Search
CPC .. C07D 487/04; C07D 519/00; C08G 61/123; C08G 61/124; C08G 61/126; C08G 2261/124; C08G 2261/1412; C08G 2261/18; C08G 2261/3223; C08G 2261/3225; C08G 2261/3241; C08G 2261/3327; C08G 2261/334; C08G 2261/344; C08G 2261/414; C08G 2261/592; C08G 2261/92; H01L 51/0036; H01L 51/0043; H01L 51/0053; H01L 51/0545; H01L 51/0558
USPC ........................................................ 526/256
See application file for complete search history.

(56) References Cited

U.S. PATENT DOCUMENTS

| 2009/0065878 A1 | 3/2009 | Li | |
| 2013/0240792 A1* | 9/2013 | Wigglesworth | .... H01L 51/0036 252/500 |
| 2014/0011973 A1* | 1/2014 | Pei | ....................... C07D 417/14 526/241 |

FOREIGN PATENT DOCUMENTS

| CN | 102775273 | * | 11/2012 | ............ H01L 51/00 |
| KR | 1020060132597 A | | 12/2006 | |
| KR | 1020090024832 A | | 3/2009 | |
| KR | 20110091711 A | | 8/2011 | |
| KR | 1020120003895 A | | 1/2012 | |
| KR | 1020120111203 A | | 10/2012 | |
| KR | 1020120084968 | * | 2/2013 | ............ C08G 61/12 |
| WO | 2013028441 A2 | | 2/2013 | |

OTHER PUBLICATIONS

ISA Korean Intellectual Property Office, International Search Report Issued in Application No. PCT/KR2013/004764, dated Dec. 24, 2013, WIPO, 5 pages.

* cited by examiner

*Primary Examiner* — Wenwen Cai
(74) *Attorney, Agent, or Firm* — McCoy Russell LLP

(57) ABSTRACT

The present invention relates to a diketopyrrolopyrrole polymer, which is an organic semiconductor compound for an organic electronic device, and a use thereof. The diketopyrrolopyrrole polymer according to the present invention is a novel organic semiconductor compound having high π-electron stacking by introducing an electron donor compound, and an organic electronic device employing the same has excellent charge mobility and on/off ratio.

2 Claims, 13 Drawing Sheets

DIKETOPYRROLOPYRROLE POLYMER AND ORGANIC ELECTRONIC DEVICE CONTAINING SAME

CROSS REFERENCE TO RELATED APPLICATIONS

The present application is a U.S. National Phase of International Patent Application Ser. No. PCT/KR2013/004764, entitled "DIKETOPYRROLOPYRROLE POLYMER AND ORGANIC ELECTRONIC DEVICE CONTAINING SAME," filed on May 30, 2013, which claims priority to Korean Patent Application No. 10-2013-0051471, entitled "DIKETOPYRROLOPYRROLE POLYMER AND ORGANIC ELECTRONIC DEVICE CONTAINING SAME," filed on May 7, 2013, the entire contents of each of which are hereby incorporated by reference for all purposes.

TECHNICAL FIELD

The present invention relates to a novel diketopyrrolopyrrole polymer and an organic electronic device containing the same, and more particularly, to a diketopyrrolopyrrole polymer, which is an organic semiconductor compound for an organic electronic device such as an organic thin film transistor (OTFT), or the like, and a use thereof.

BACKGROUND ART

In accordance with the development of 21C information and communication technologies and a desire for a personal portable communication device, a micromachining process enabling an information and communication device having a small size, a light weight, and a thin thickness, and capable of being easily used, a high-performance electric and electronic material capable of manufacturing an ultra high density integrated circuit, and a novel information and communication material capable of implementing a new concept display have been required. Among them, since an organic thin film transistor (OTFT) may be used as an important component of display drivers of portable computers, organic electro luminescence devices, smart cards, electric tags, pagers, mobile phones, or the like, and plastic circuit parts of memory devices such as automated teller machines, identification tags, or the like, etc., the organic thin film transistor (OTFT) has been the subject of various studies.

The organic thin film transistor using an organic semiconductor has advantages such as a simple manufacturing process and low production cost as compared to organic thin film transistors using amorphous silicon and polysilicon up to now, excellent compatibility with plastic boards for implementing flexible displays, or the like. Therefore, recently, various researches into the organic thin film transistor using an organic semiconductor have been conducted. Particularly, since a thin film may be easily formed by a solution process in a case of using a polymer organic semiconductor, manufacturing cost may be decreased as compared to a small molecular organic semiconductor compound.

As a representative semiconductor compound for a polymer based organic thin film transistor developed up to now, there are poly(3-hexylthiophene) (P3HT) and poly(9,9-dioctylfluorene-co-bithiophene) (F8T2). The OTFT has various performances, but among them, important evaluation barometers are charge mobility and an on/off ratio. Among them, the most important evaluation barometer is the charge mobility. The charge mobility is different depending on the kind of semiconductor material, a formation method (structure and morphology) of a thin film, a driving voltage, or the like.

FIG. 1 is a cross-sectional view of a general organic thin film transistor composed of a substrate/gate/insulating layer/electrode layer (source, drain)/organic semiconductor layer. Referring to FIG. 1, a gate electrode is formed on the substrate. The insulating layer is formed on the gate electrode, and the organic semiconductor layer and source and drain electrodes are sequentially formed thereon. The driving principle of the organic thin film transistor having the above-mentioned structure will be described below with an example of a p-type semiconductor. First, in the case of applying a voltage between a source and a drain to flow a current, a current in proportion to the voltage flows at a low voltage. Here, when a positive voltage is applied to a gate, all holes, which are positive charges, are pushed toward an upper portion of the semiconductor layer by an electric field due to the applied voltage. Therefore, a depletion layer in which there is no conductive charge is formed in a portion adjacent to the insulating layer, and even though a voltage is applied between the source and the drain, since conductive charge carriers are decreased in this situation, a low amount of current will flow. On the contrary, when a negative voltage is applied to the gate, an accumulation layer in which positive charges are induced is formed in a portion adjacent to the insulating layer by an effect of the electric field due to the applied voltage. In this case, since a large amount of conductive charge carrier is present between the source and the drain, a larger amount of current may flow. Therefore, a current flowing between the source and the drain may be controlled by alternatively applying the positive voltage and the negative voltage to the gate in a state in which the voltage is applied between the source and the drain.

Examples of components used in the organic thin film transistor configured as described above include electrodes (source and drain), a substrate and a gate electrode, which are required to have high thermal stability, an insulator required to have high insulation properties and dielectric constant, a semiconductor smoothly moving charges, and the like. Among them, a core material having many problems to overcome is an organic semiconductor. The organic semiconductor may be divided into a small molecular organic semiconductor and a polymer organic semiconductor depending on a molecular weight thereof, and may be classified into an n-type organic semiconductor and a p-type organic semiconductor depending on whether or not the organic semiconductor transports electrons or holes. Generally, in the case of using a small molecular organic semiconductor at the time of forming an organic semiconductor layer, since the small molecular organic semiconductor may be easily purified and thus impurities may be almost removed, charge transfer properties may be excellent. However, since it is impossible to perform spin-coating or printing, a thin film should be manufactured by a vacuum deposition method, such that a manufacturing process is complicated and expensive as compared to the polymer organic semiconductor. In the case of the polymer organic semiconductor, it is difficult to purify the polymer organic semiconductor with a high purity, but thermal resistance is excellent, and it is possible to perform spin-coating and printing, such that the polymer organic semiconductor has advantages in view of a manufacturing process, cost, and mass production.

In order to develop organic semiconductor materials, many studies have been conducted up to now, but the development of polymer based semiconductor materials is still far below the development of small molecule based semiconductor materials. Therefore, in order to develop an electronic device using an organic thin film transistor which is flexible and is cheaply manufactured, the development of a polymer based semiconductor material has been urgently demanded. Generally, it is known that charge mobility of a polymer is lower than that of a small molecule, but the polymer may be a material capable of sufficiently overcoming this disadvantage in view of a manufacturing process or cost.

A polymer in which an S containing heteroaromatic ring is directly bound to a diketopyrrolopyrrole group has been disclosed in Korean Patent Laid-Open Publication Nos. 2011-0091711 and 2009-0024832. However, since sufficient expansion of π-electron is not still exhibited, the development of a polymer semiconductor material exhibiting sufficient π-electron stacking has been required.

DISCLOSURE

Technical Problem

An object of the present invention is to provide a diketopyrrolopyrrole polymer including a double bond, which has high thermal stability by alternately polymerizing a diketopyrrolopyrrole derivative, one of the electron acceptor materials, and an aromatic or heteroaromatic compound linked through a vinylene bond, an electron donor material, and may exhibit sufficient π-electron expansion by increasing coplanarity of a main chain and allowing the diketopyrrolopyrrole polymer to have an expanded conjugation structure.

Another object of the present invention is to provide a diketopyrrolopyrrole polymer, which is an organic semiconductor compound of which spin coating may be easily performed at room temperature due to high solubility and viscosity caused by a high molecular weight, and thus a solution process may be performed.

Another object of the present invention is to provide a diketopyrrolopyrrole polymer, which is an organic semiconductor compound having high charge mobility capable of being applied to an organic electronic device.

Another object of the present invention is to provide an organic electronic device containing a novel diketopyrrolopyrrole polymer according to the present invention.

Technical Solution

The present invention relates to a diketopyrrolopyrrole polymer, which is an organic semiconductor compound for an organic electronic device, and a use thereof. More particularly, the present invention relates to a diketopyrrolopyrrole polymer, which is a p-type polymer organic semiconductor compound configured so that a diketopyrrolopyrrole derivative, an electronic acceptor compound, and a compound including a vinylene group, an electron donor compound, are alternately polymerized, and used as a material of an active layer of an organic thin film transistor, and an organic electronic device containing the same.

In one general aspect, a novel diketopyrrolopyrrole polymer may be represented by the following Chemical Formula 1.

[Chemical Formula 1]

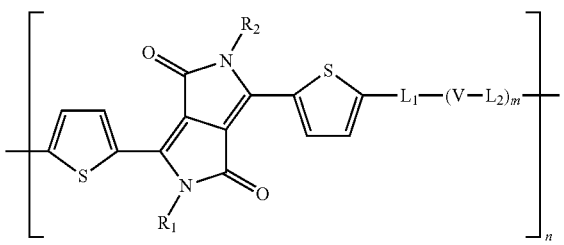

[In Chemical Formula 1, $R_1$ and $R_2$ are

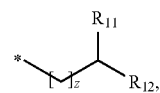

$R_{11}$ and $R_{12}$ are each independently (C10-C50)alkyl, and z is an integer of 3 to 20;

$L_1$ and $L_2$ are each independently selected from the following structures;

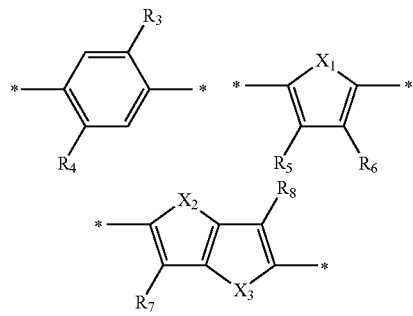

V is

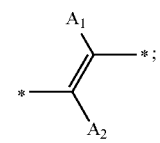

$X_1$ to $X_3$ are each independently Se, O, NH, or NR';

$A_1$ and $A_2$ are each independently hydrogen, cyano, or —COOR";

R' and R" are each independently (C1-C50)alkyl or (C6-C50)aryl;

$R_3$ to $R_8$ are each independently hydrogen, hydroxyl, amino, (C1-C50)alkyl, (C6-C50)aryl, (C1-C50)alkoxy, mono- or di-(C1-C50)alkylamino, (C1-C50)alkoxycarbonyl, or (C1-C50)alkylcarbonyloxy;

m is an integer of 1 or 2, and when m is 2, each of the V and $L_2$ are the same as or different from each other; and n is an integer of 1 to 1,000.]

In the diketopyrrolopyrrole polymer according to the present invention, represented by Chemical Formula 1, electron density is improved by introducing the vinylene group V into the diketopyrrolopyrrole derivative to increase coplanarity of a main chain and allow the diketopyrrolopyrrole polymer to have an expanded conjugation structure, and thus intermolecular interactions are increased. Therefore, the organic electronic device containing the diketopyrrolopyrrole polymer may have high mobility.

In addition, the diketopyrrolopyrrole polymer has a structure in which $R_1$ and $R_2$, substituents of the diketopyrrolopyrrole derivative, are

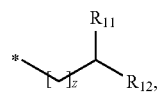

such that the diketopyrrolopyrrole polymer may have higher solubility. That is, the diketopyrrolopyrrole polymer has a structure in which z(s) of $R_1$ and $R_2$ are integers of 3 to 10, preferably 6 to 8, and $R_1$ and $R_2$ have branched chain alkyl at ends thereof, such that the diketopyrrolopyrrole polymer has high solubility while having charge mobility at least 10 times higher than that of an alkyl that does not have a branched chain at an end thereof. Therefore, the diketopyrrolopyrrole polymer may be more advantageous in a solution process, and a large area organic electronic device may be manufactured through a simple and cheap process.

In Chemical Formula 1, $-L_1-(V-L_2)_m-$ may be selected from the following structures.

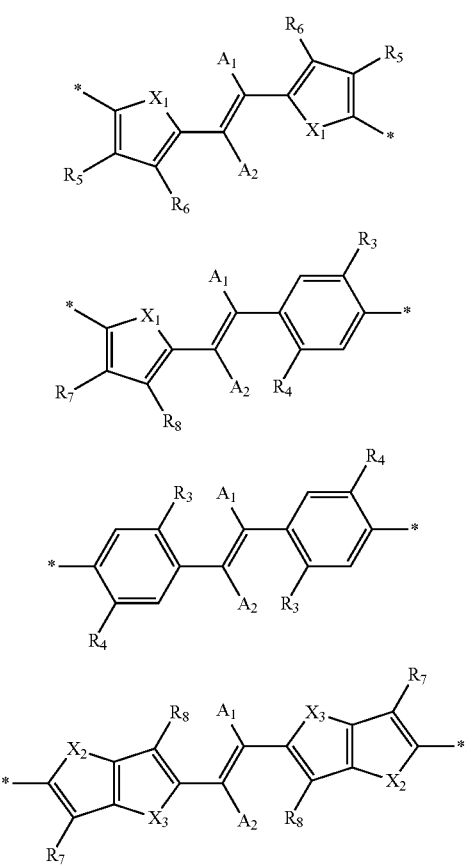

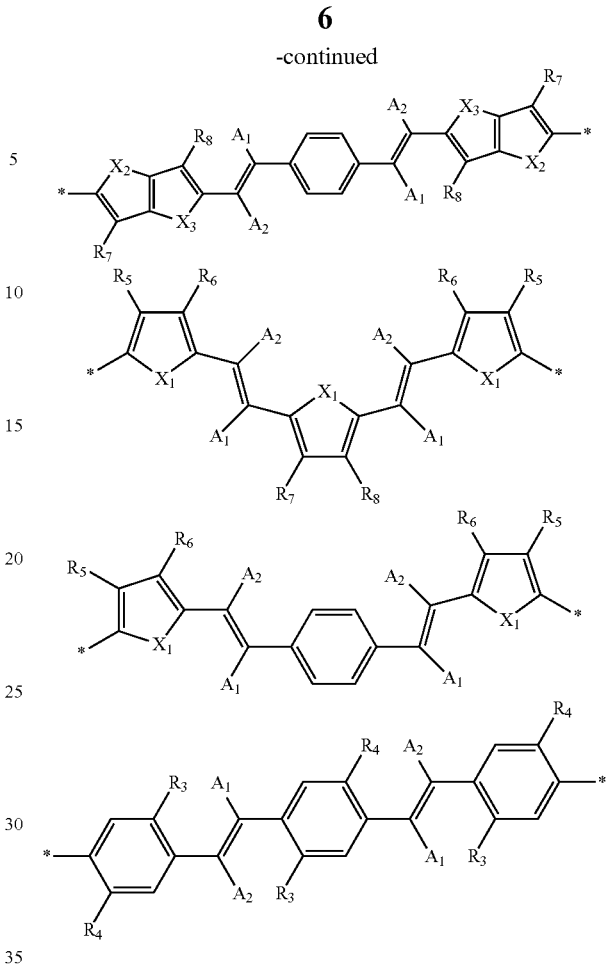

[$X_1$, $X_2$, $X_3$, $A_1$, $A_2$, $R_3$, $R_4$, $R_5$, $R_6$, $R_7$, and $R_8$ have the same definitions as described above].

In more detail, $-L_1-(V-L_2)_m-$ may be selected from the following structures.

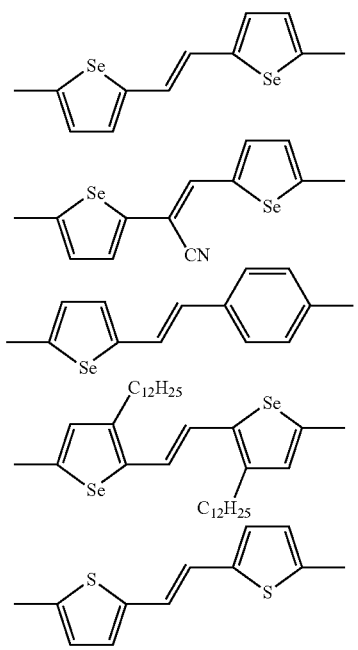

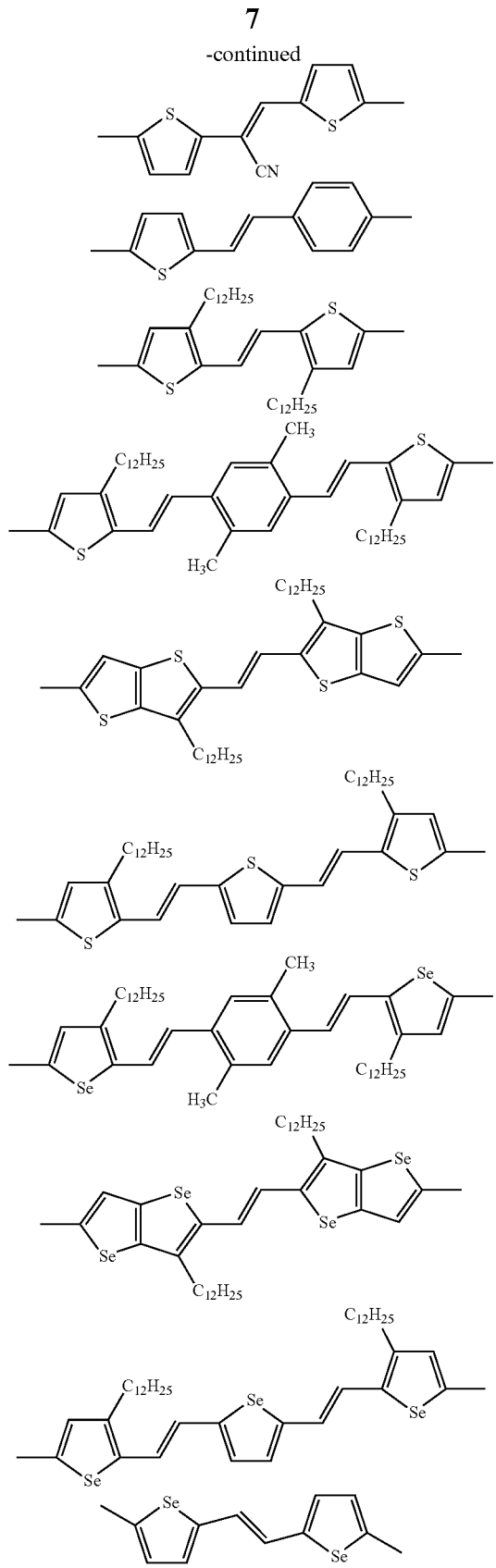
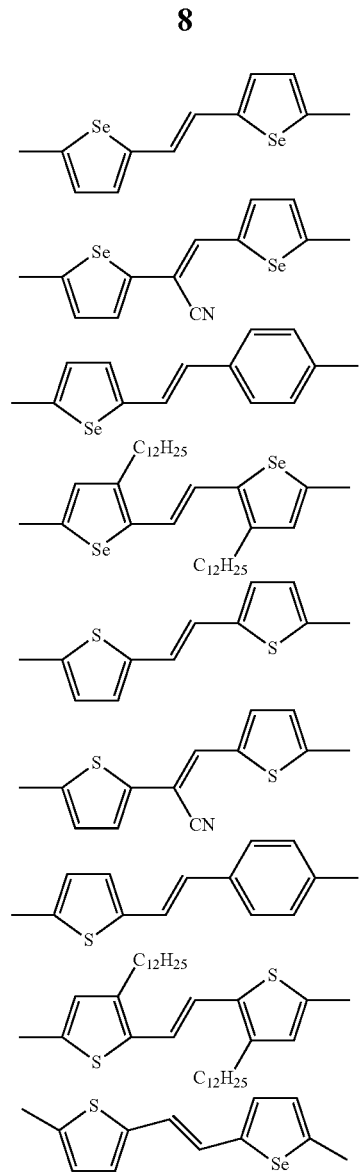

In the diketopyrrolopyrrole polymer according to the exemplary embodiment of the present invention, represented by Chemical Formula 1, more preferably, in view of having excellent charge mobility and on/off ratio while having high solubility, -L$_1$-(V-L$_2$)$_m$- may be selected from the following structures,

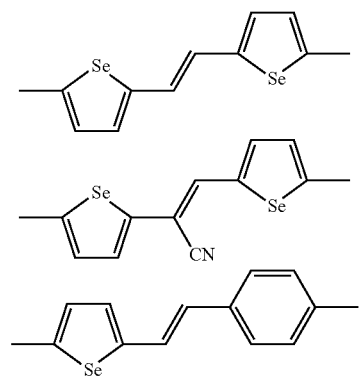

In Chemical Formula 1, in view of having excellent charge mobility and on/off ratio, more preferably, -L$_1$-(V-L$_2$)$_m$- may be selected from the following structures.

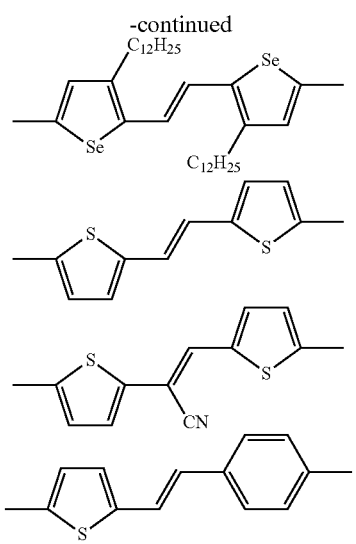
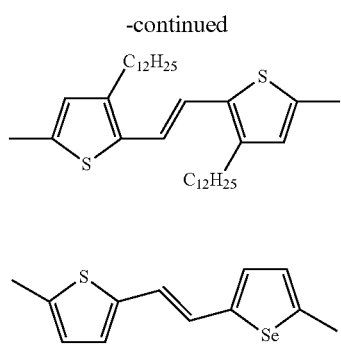
$R_{11}$ and $R_{12}$ being each independently (C20-C50)alkyl, more preferably (C22-C50)alkyl.
The polymer according to the exemplary embodiment of the present invention may be selected from the following compounds, but is not limited thereto.
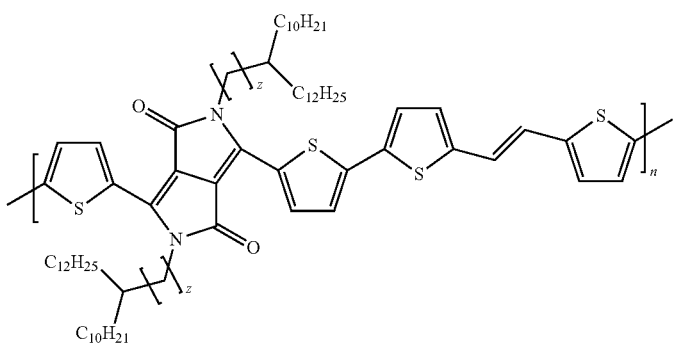
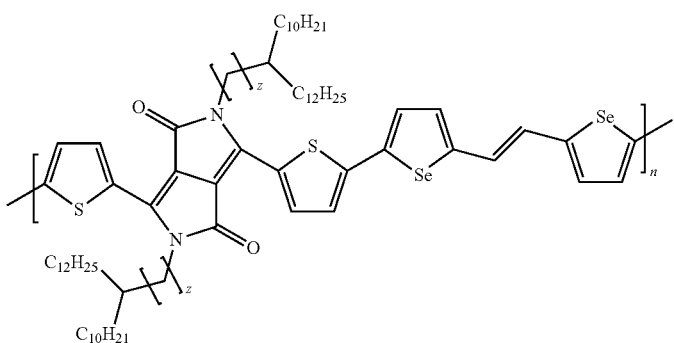
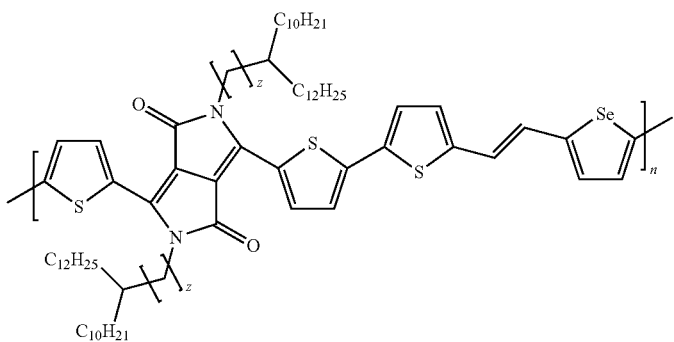

-continued
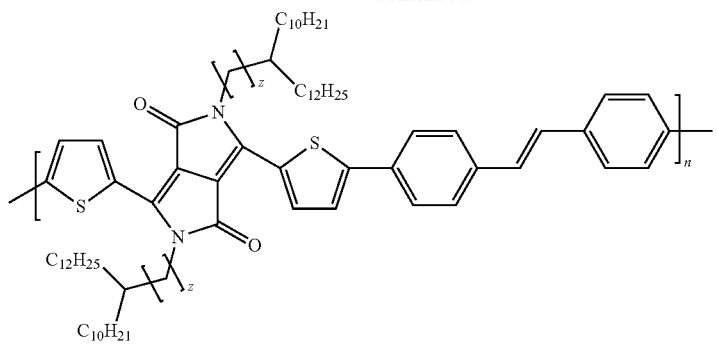
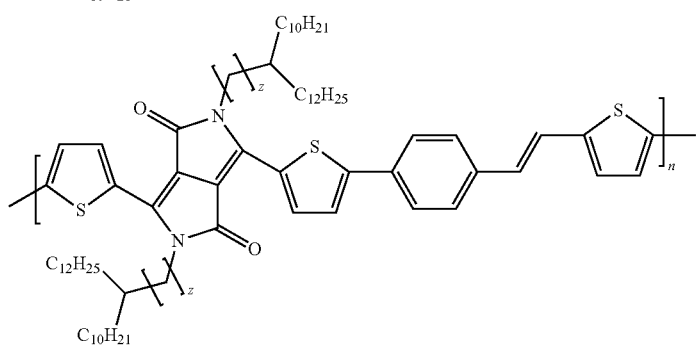
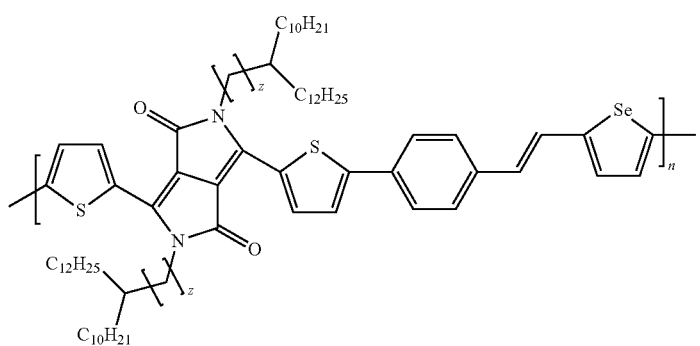
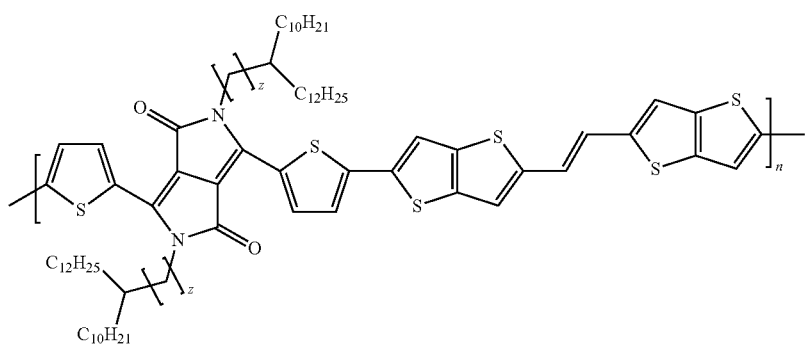
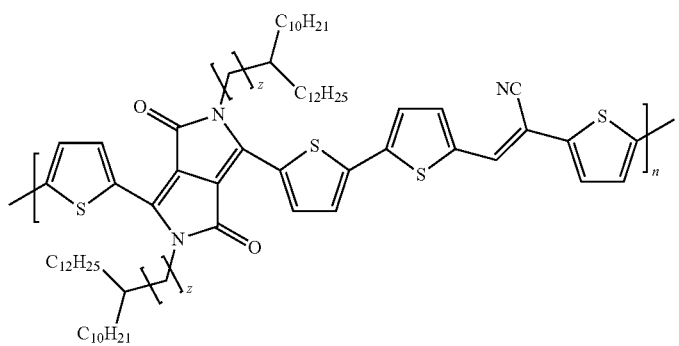

-continued

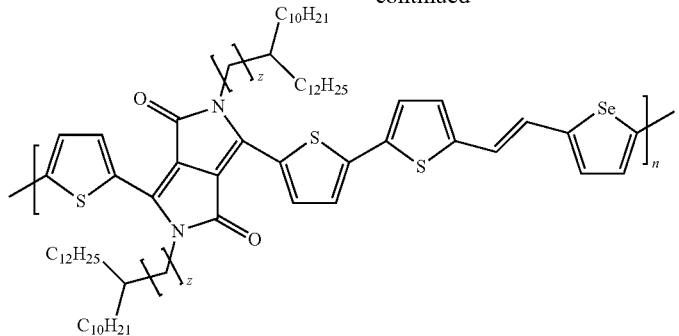

[z is an integer of 3 to 20; and
n is an integer of 1 to 1,000.]

More specifically and preferably, in view of having excellent charge mobility and on/off ratio while having high solubility, the diketopyrrolopyrrole polymer according to the exemplary embodiment of the present invention may be the following compound.

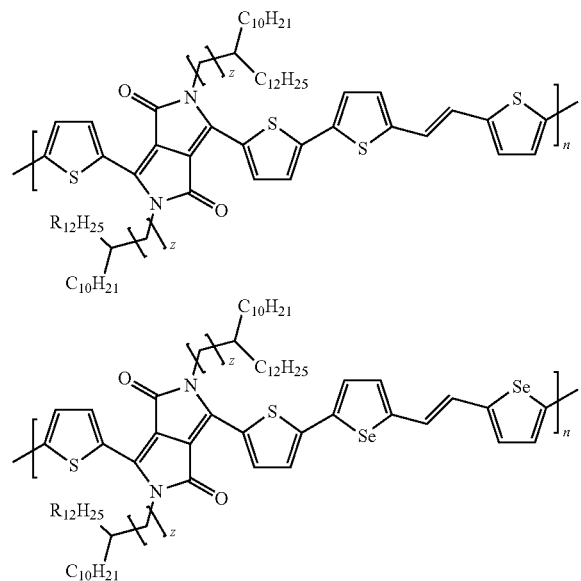

[z is an integer of 6 to 8; and
n is an integer of 1 to 1,000.]

That is, more specifically, when the diketopyrrolopyrrole polymer according to the present invention has a structure in which $R_1$ and $R_2$ of Chemical Formula 1 are alkyls having at least 22 carbon atoms, straight chains of the alkyls have 6 to 8 carbon atoms, and $R_1$ and $R_2$ have branched chain alkyls at the end thereof, the diketopyrrolopyrrole polymer has high solubility, but the charge mobility or on/off ratio is not changed, such that the organic electronic device containing the diketopyrrolopyrrole polymer may have high efficiency.

As a method of preparing the diketopyrrolopyrrole polymer according to the present invention, a final compound may be prepared through an alkylation reaction, a Grignard coupling reaction, a Suzuki coupling reaction, a Stille coupling reaction, or the like. A method of preparing the organic semiconductor compound according to the present invention is not limited to the above-mentioned method, but the organic semiconductor compound may be prepared by a general organic chemical reaction.

In addition, the diketopyrrolopyrrole polymer according to the present invention may be used as a material for forming an organic semiconductor layer of an organic electronic device, therefore the present invention provides an organic electronic device containing a diketopyrrolopyrrole polymer.

In particular, the organic electronic device according to the present invention may be an organic thin film transistor, and a specific example of a manufacturing method of the organic thin film transistor according to the present invention is as follows.

It is preferable that an n-type silicon substrate used in a general organic thin film transistor is used as a substrate 11. A function of a gate electrode is included in this substrate. As the substrate, a glass substrate or transparent plastic substrate having excellent surface smoothness, handling easiness, and water-proofing performance may also be used as well as the n-type silicon substrate. In this case, a gate electrode needs to be added onto the substrate. Examples of a material applicable to the substrate may include glass, polyethylenenaphthalate (PEN), polyethylene terephthalate (PET), polycarbonate (PC), polyvinylalcohol (PVA), polyacrylate, polyimide, polynorbornene, and polyethersulfone (PES).

As a gate insulating layer 12 constituting the OTFT device, an insulator having high permittivity, which is generally used, may be used. In detail, a ferroelectric insulator selected from the group consisting of $Ba_{0.33}Sr_{0.66}TiO_3$ (BST), $Al_2O_3$, $Ta_2O_5$, $La_2O_5$, $Y_2O_3$, and $TiO_2$, an inorganic insulator selected from the group consisting of $PdZr_{0.33}Ti_{0.66}O_3$(PZT), $Bi_4Ti_3O_{12}$, $BaMgF_4$, $SrBi_2(TaNb)_2O_9$, $Ba(ZrTi)O_3$(BZT), $BaTiO_3$, $SrTiO_3$, $Bi_4Ti_3O_{12}$, $SiO_2$, $SiN_x$, and AlON, or an organic insulator such as polyimide, benzocyclobutene (BCB), parylene, polyacrylate, polyvinylalcohol, and polyvinylphenol, and the like, may be used.

A configuration of the organic thin film transistor according to the present invention may all include a bottom-contact type, consisting of a substrate/gate electrode/insulating layer/source and drain electrodes/organic semiconductor layer, as well as a top-contact type, consisting of a substrate 11/gate electrode 16/insulating layer 12/organic semiconductor layer 13/source and drain electrodes 14 and 15 as illustrated in FIG. 1. Further, as a surface treatment method, 1,1,1,3,3,3-hexamethyldisilazane (HMDS), octadecyltrichlorosilane (OTS), or octadecyltrichlorosilane (OTDS) may be coated or may not be coated between the source and drain electrodes 14 and 15 and the organic semiconductor layer 13.

The organic semiconductor layer using the diketopyrrolopyrrole polymer according to the present invention may be formed in a thin film form by a vacuum deposition method, a screen printing method, a printing method, a spin casting method, a spin coating method, a dipping method, or an ink spraying method. In this case, deposition of the organic semiconductor layer may be performed using a high temperature solution at 40° C. or more, and a preferable thickness of the organic semiconductor layer is 500Å or so.

The gate electrode 16 and the source and drain electrodes 14 and 15 may be made of any conductive material, but it is preferable that the gate electrode 16 and the source and drain electrodes 14 and 15 are made of a material selected from the group consisting of gold (Au), silver (Ag), aluminum (Al), nickel (Ni), chromium (Cr), and indium tin oxide (ITO).

Advantageous Effects

A diketopyrrolopyrrole polymer according to the present invention is configured so that a diketopyrrolopyrrole derivative, an electron acceptor compound, and a compound containing a vinylene group, electron donor compound, are alternately polymerized. Further, in the diketopyrrolopyrrole polymer, electron density may be improved by introducing the vinylene group to increase coplanarity of a main chain and allow the diketopyrrolopyrrole polymer to have an expanded conjugation structure, such that intermolecular interactions may be increased and excellent thermal stability may be exhibited.

Further, the diketopyrrolopyrrole polymer according to the present invention has a property that a highest occupied molecular orbital (HOMO) value is decreased, that is, the diketopyrrolopyrrole polymer has excellent charge mobility and oxidation stability due to an increase in electron density in a repeat unit, such that the diketopyrrolopyrrole polymer may be significantly usefully applied to an organic semiconductor layer of an organic thin film transistor.

Further, an organic electronic device according to the present invention uses the diketopyrrolopyrrole polymer according to the present invention, such that charge mobility and an on/off ratio are improved, and thus, the organic electronic device may have excellent efficiency and performance.

Furthermore, in order to allow the diketopyrrolopyrrole polymer according to the present invention to have high solubility without affecting other electrical properties, a substituent, that is, a substituent of which the number of carbon atoms and a shape are limited is introduced into N of diketopyrrolopyrrole, such that the organic electronic device containing the diketopyrrolopyrrole polymer according to the present invention may be manufactured by vacuum deposition or a solution process such as spin coating or printing. Therefore, a large-area organic electronic device may be manufactured by a simple and cheap process.

BEST MODE

Figure 1:
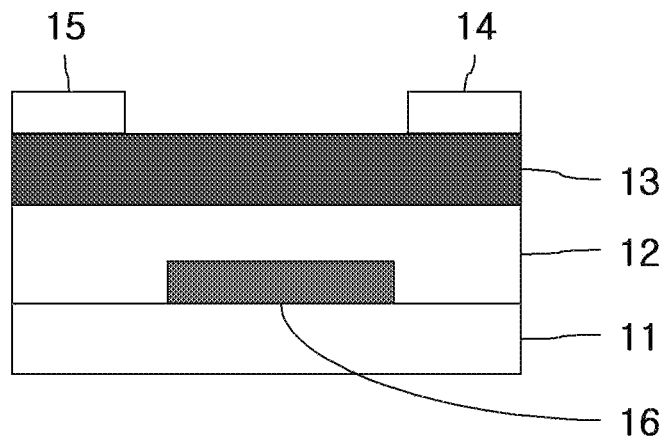
FIG. 1 is a cross-sectional view illustrating a structure of a general organic thin film transistor composed of a substrate/gate/insulating layer (source, drain)/semiconductor layer (11: substrate, 12: insulating layer, 13: channel material, 14: source, 15: drain, 16: gate).

The present invention will be understood and appreciated more fully from the following Examples, and the Examples are for illustrating the present invention and not for limiting the present invention.

EXAMPLE 1

Synthesis of 7-decyl-1-nonadecylbromide

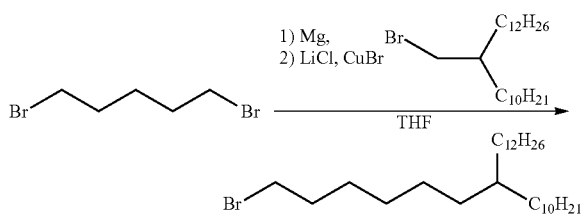

A Grignard reagent was prepared by slowly adding 2-decyl-1-tetradecylbromide (30.0 g, 0.072 mol) and magnesium (Mg, 2.40 g, 0.101 mol) to a solvent, tetrahydrofuran (THF, 100 ml), and then, slowly added to a mixed solution of 1,5-dibromopentane (38.0 g, 0.165 mol), copper bromide (CuBr, 0.1 g, 0.72 mmol), and lithium chloride (LiCl, 0.06 g, 1.44 mmol) at −0° C. After reaction at room temperature for 24 hours, the resultant was extracted with a solvent, diethyl ether, dried over magnesium sulfate (MgSO$_4$), and then, filtered. After removing the solvent, 1,5-dibromopentane was separated using a distiller, and the resultant was purified by column chromatography using hexane as a solvent, thereby obtaining a target compound, 7-decyl-1-nonadecylbromide (28 g, yield: 80%).

$^1$HNMR (CDCl$_3$, 300 MHz) [ppm]: δ3.76 (d, 2H), 1.88 (d, 2H), 1.4 (s, 1H), 1.26-1.24 (m, 48H), 0.92-0.88 (m, 6H).

EXAMPLE 2

Synthesis of 2,5-bis(2-decylnonadecyl)-3,6-bis(thiophen-2-yl)-pyrrolo[3,4-c]pyrrole-1,4(2H,5H)-dione

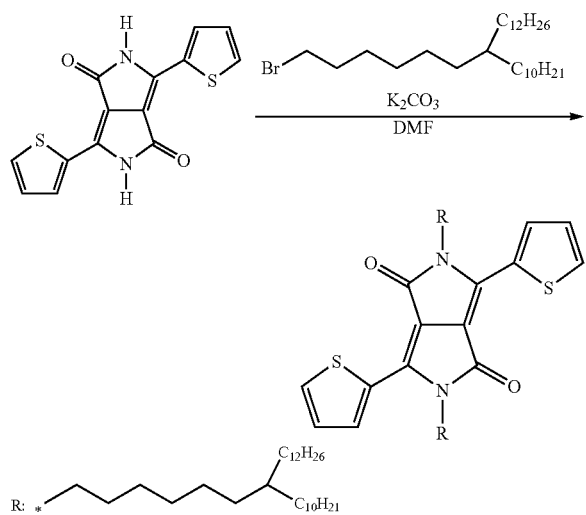

After 3,6-di(thiophen-2-yl)pyrrolo[3,4-c]pyrrole-1,4(2H,5H)-dione (DPP, 1.00 g, 0.003 mol) and potassium carbonate (K$_2$CO$_3$, 1.84 g, 0.012 mol) were put into a flask and dissolved in a solvent, dimethylformamide (DMF, 60 ml), a temperature was raised to 150° C., and the mixture was stirred for 6 hours. In addition, 7-decyl-1-nonadecylbromide (8 g, 0.012 mol) was added thereto in portions, and stirred for 16 hours under nitrogen atmosphere. The resultant was extracted with a solvent, diethyl ether, dried over magnesium sulfate (MgSO$_4$), and then, filtered. The resultant was separated by column chromatography using hexane/methylene chloride (1:3) as a solvent, thereby obtaining a title compound (1.2 g, yield: 37%).

$^1$H-NMR (300 MHz, CDCl$_3$, ppm): δ8.96 (d, 2H), 7.64 (d, 2H), 7.32 (d, 2H), 4.11-4.06 (t, 4H), 1.81-1.72 (t, 4H), 1.44-1.27 (m, 98H), 0.92-0.81 (m, 12H), $^{13}$C-NMR (125 MHz, CDCl$_3$, ppm): 161.78, 140.42, 135.62, 130.97, 130.22, 128.98, 108.16, 42.65, 37.82, 34.10, 32.32, 30.55, 30.39, 30.113, 30.054, 29.75, 27.34, 27.12, 27.05, 23.08, 14.49.

EXAMPLE 3

Synthesis of 3,6-bis(5-bromothiophen-2-yl)-2,5-bis(2-decylnonadecyl)-pyrrolo[3,4-c]pyrrole-1,4(2H,5H)-dione

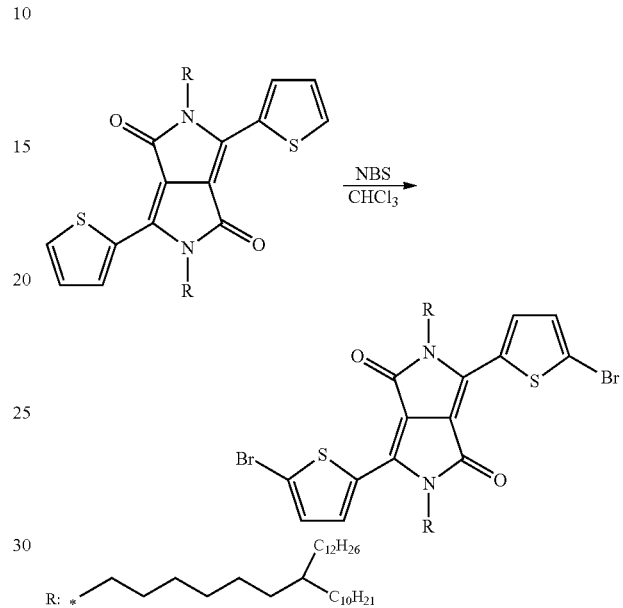

After 2,5-bis(2-decylnonadecyl)-3,6-bis(thiophen-2-yl)-pyrrolo[3,4-c]pyrrole-1,4(2H,5H)-dione 1.2 g, 0.85 mmol) was dissolved in chloroform (40 ml) in a flask, light was blocked using aluminum foil, or the like. Thereafter, NBS (0.5 g, 1.75 mmol) was slowly added dropwise thereto and stirred for 8 hours. The resultant was extracted with MC, and an organic layer was washed with water and dried over MgSO$_4$, followed by removal of a solvent using a rotary evaporator. The resultant was separated by column chromatography using n-hexane/EA (15:1) as a solvent and recrystallized with MC and hexane, thereby obtaining a title compound (1.2 g, yield: 80%).

$^1$H-NMR (300 MHz, CDCl$_3$, ppm): δ 8.71 (d, 2H), 726 (d, 2H), 4.02-3.97 (t, 4H), 1.78-1.71 (t, 4H), 1.44-1.2 (m, 98H), 0.92-0.87 (m, 12H), $^{13}$C-NMR (125 MHz, CDCl$_3$, ppm): 161.43, 139.38, 135.72, 132.04, 131.56, 119.50, 108.26, 4271, 37.82, 34.09, 3232, 30.56, 30.41, 30.11, 30.05, 29.75, 27.28, 27.12, 27.01, 23.08, 14.49.

EXAMPLE 4

Synthesis of P-29-DPPDBTE

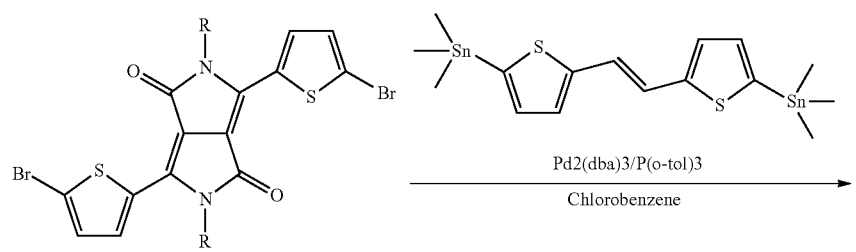

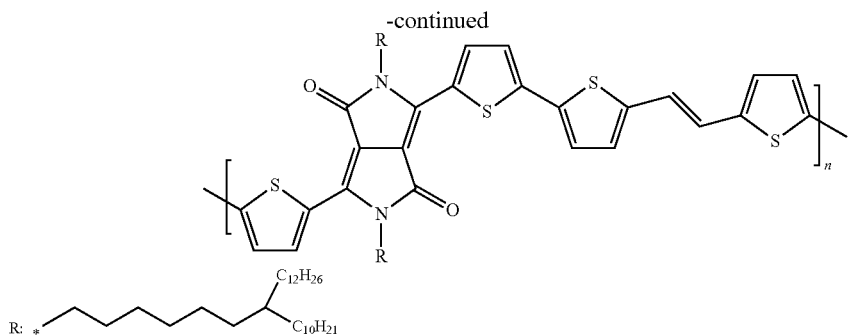

P-29-DPPDBTE corresponding to the polymer may be polymerized by a Stille coupling reaction 3,6-bis(5-bromo-thiophen-2,5-bis(2-decylnonadecyl)-pyrrolo[3,4-c]pyrrole-1,4(2H,5H)-dione (0.50 g, 0.39 mmol) and (E)-1,2-bis(5-(trimethylstannyl)thiophen-2-yl)ethene (0.229 g, 0.39 mmol) were dissolved in chlorobenzene (5 mL), and nitrogen substation was performed. Thereafter, $Pd_2(dba)_3$ (0.007 g, 2 mol %) and $P(o\text{-tol})_3$ (0.011 g, 8 mol %) were added thereto as catalysts, and the mixture was refluxed at 100° C. for 48 hours. Then, the reaction solution was slowly precipitated in methanol (300 mL), and a formed solid was filtered. The filtered solid was purified sequentially with methanol, hexane, toluene, and chloroform through a sohxlet. A dropped liquid was precipitated in methanol again, filtered using a filter, and dried, thereby obtaining a title compound, P-29-DPPDBTE (yield: 90%), as a dark green solid.

0.52 g. (Mn=33,369, Mw=60,781, PDI=1.82).

$^1$H NMR ($CDCl_3$, 500 MHz), δ(ppm): δ8.96 (broad, 4H), 7.1 (broad, 2H), 6.75 (broad, 4H), 4.01 (broad, 4H), 1.25 (broad, 98H), 0.85 (broad, 12H).

EXAMPLE 5

Synthesis of P-29-DPPDTSE

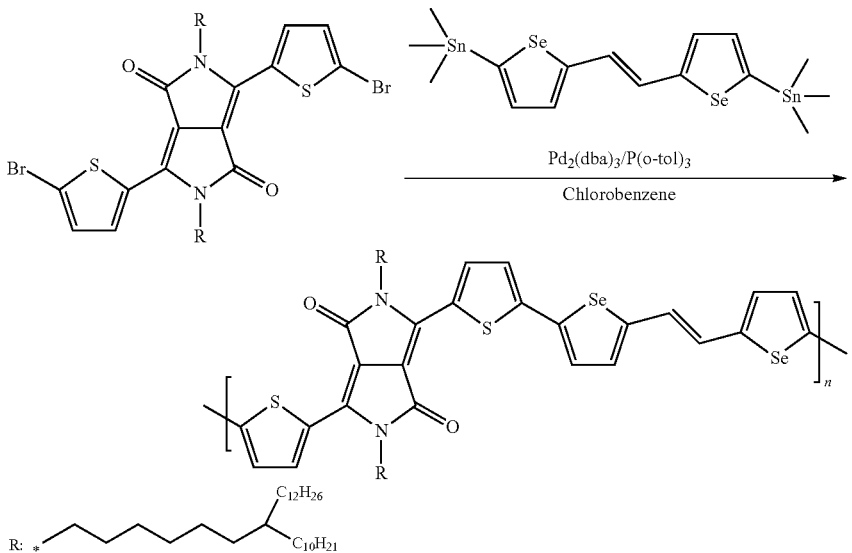

P-29-DPPDTSE corresponding to the polymer may be polymerized by a Stille coupling reaction. P-29-DPPDTSE corresponding to a title compound was obtained (yield: 80%) by the same method as in Example 4 except for using 3,6-bis(5-bromothiophen-2-yl)-2,5-bis(2-decylnonadecyl)-pyrrolo[3,4-c]pyrrole-1,4(2H,5H)-dione (0.500 g, 0.39 mmol), (E)-1,2-bis(5-(trimethylstannyl)selenophen-2-yl)ethene (0.229 g, 0.39 mmol), $Pd_2(dba)_3$ (0.007 g, 2 mol %), and $P(o\text{-tol})_3$ (0.011 g, 8 mol %).

0.49 g. (Mn=35,826, Mw=58,038, PDI=1.62).

$^1$H NMR ($CDCl_3$, 500 MHz), δ(ppm): δ8.78 (broad, 4H), 7.21 (broad, 2H), 6.75 (broad, 4H), 4.02 (broad, 4H), 1.26 (broad, 98H), 0.85 (broad, 12H).

EXAMPLE 6

Manufacturing of Organic Electron Device

An OTFT device was manufactured in a top-contact manner, n-doped silicon (100 nm) was used as a gate, and $SiO_2$ was used as an insulator. At the time of surface treatment, after a surface was washed using piranha cleaning solution ($H_2SO_4:2H_2O_2$), self-assemble monolayer (SAM) treatment was performed thereon using octadecyltrichlorosilane (OTS-18, Alfa Corp.). An organic semiconductor layer was coated with chloroform solution (0.2 wt %) at a rate of 2000 rpm for 1 minute using a spin-coater. As an organic semiconductor material, P-29-DPPDBTE and P-29-DPP-DTSE synthesized in Examples 4 and 5 were used. Gold used as a source and a drain was deposited at 1 A/s so as to have a thickness of 100 nm. A length of a channel was 15 μm and a width thereof was 1500 μm. Properties of the OTFT were measured using Keithley 4800.

Charge mobility was obtained from a slope of a graph obtained using $(I_{SD})^{1/2}$ and $V_G$ as variables from the following Saturation Region Current Equation.

$$I_{SD} = \frac{WC_0}{2L}\mu(V_G - V_T)^2$$

$$\sqrt{I_{SD}} = \sqrt{\frac{\mu WC_0}{2L}}(V_G - V_T)$$

$$\text{slope} = \sqrt{\frac{\mu WC_0}{2L}}$$

$$\mu_{FET} = (\text{slope})^2 \frac{2L}{WC_0}$$

In Saturation Region Current Equation, $I_{SD}$ is a source-drain current, $\mu$ or $\mu_{FET}$ is charge mobility, $C_0$ is capacitance of an oxide film, W is a width of a channel, L is a length of the channel, $V_G$ is a gate voltage, $V_T$ is a threshold voltage. Further, an off current $I_{off}$ is a current flowing in an off state. The off current was obtained as a minimum current from a current ratio in an off state.

Figure 2:
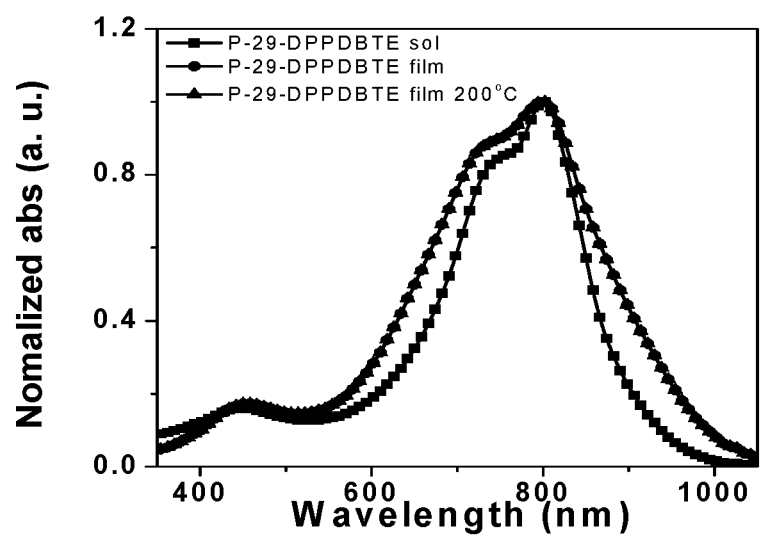
FIG. 2 illustrates UV-vis absorption spectra of a diketopyrrolopyrrole polymer P-29-DPPDBTE according to Example 4 in a solution state and a film state.
Figure 3:
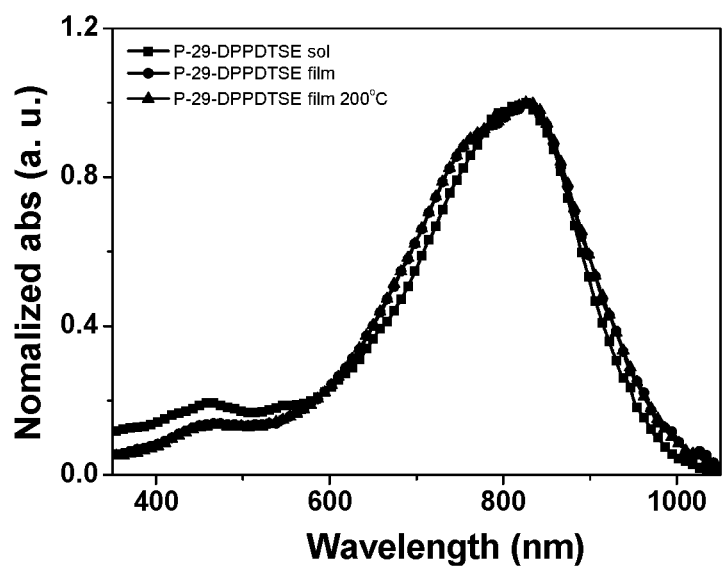
FIG. 3 illustrates UV-vis absorption spectra of a diketopyrrolopyrrole polymer P-29-DPPDTSE according to Example 5 in a solution state and a film state.
Figure 4:
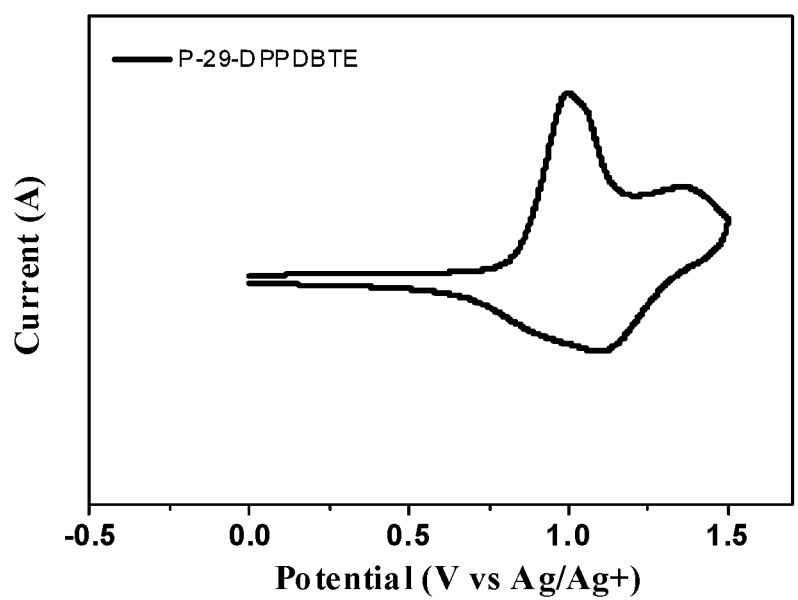
FIG. 4 is a graph illustrating electrical properties (cyclic voltammetry) of the diketopyrrolopyrrole polymer P-29-DPPDBTE according to Example 4.
Figure 5:
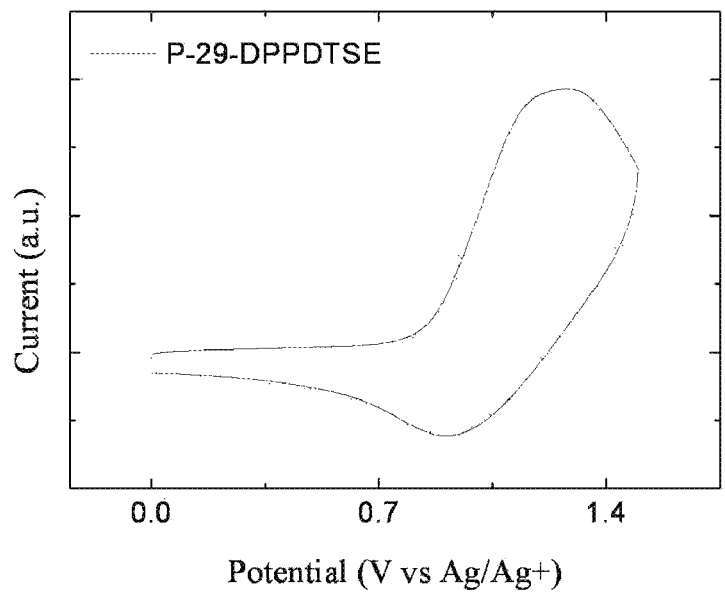
FIG. 5 is a graph illustrating electrical properties (cyclic voltammetry) of the diketopyrrolopyrrole polymer P-29-DPPDTSE according to Example 5.

Light absorption regions of novel diketopyrrolopyrrole polymers (P-29-DPPDBTE and P-29-DPPDTSE) synthesized in Examples 4 and 5 were measured in a solution state and a film state, and the results were illustrated in FIGS. 2 and 3. In order to analyze electrochemical properties of the novel diketopyrrolopyrrole polymers P-29-DPPDBTE and P-29-DPPDTSE), which were organic semiconductor compounds synthesized in Examples 4 and 5, results obtained by measuring electrochemical properties of the novel diketopyrrolopyrrole polymers (P-29-DPPDBTE and P-29-DPPDTSE) at 50 mV/s in a solvent of $Bu_4NClO_4$ (0.1 molar concentration) using cyclic voltammetry were illustrated in FIGS. 4 and 5. At the time of measurement, a voltage was applied through coating using a carbon electrode.

Optical and electrochemical properties of the diketopyrrolopyrrole polymers (P-29-DPPDBTE and P-29-DPPDTSE) synthesized in Example 4 and Example 5 were illustrated in the following Table 1. Here, HOMO values were values calculated using measurement values in FIGS. 4 and 5. In addition, band gap values were obtained from UV absorption wavelengths in the film state.

As illustrated in FIGS. 6 and 7 and FIGS. 8 and 9, it may be appreciated that thermal stability of the organic semiconductor compounds synthesized according to the present invention was excellent, and charge mobility was increased at the time of annealing, such that the organic semiconductor compounds were excellent materials for an organic electronic device.

Figure 10:
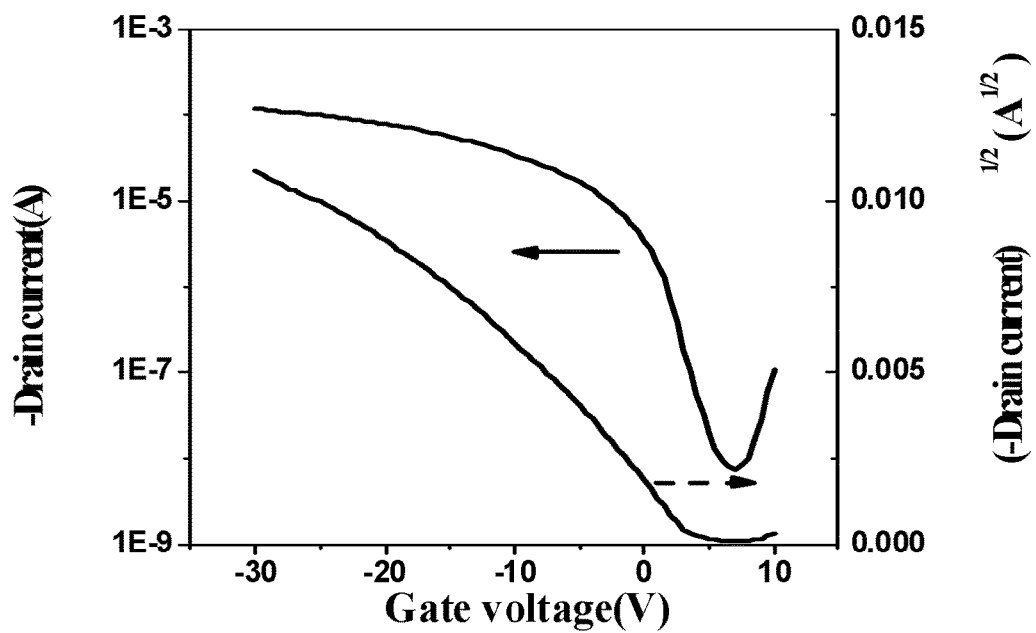
FIGS. 10 and 11 are graphs illustrating properties (transfer curve, output curve) of a device manufactured using a diketopyrrolopyrrole polymer (P-29-DPPDBTE) according to Example 4 by a method of Example 6.
Figure 11:
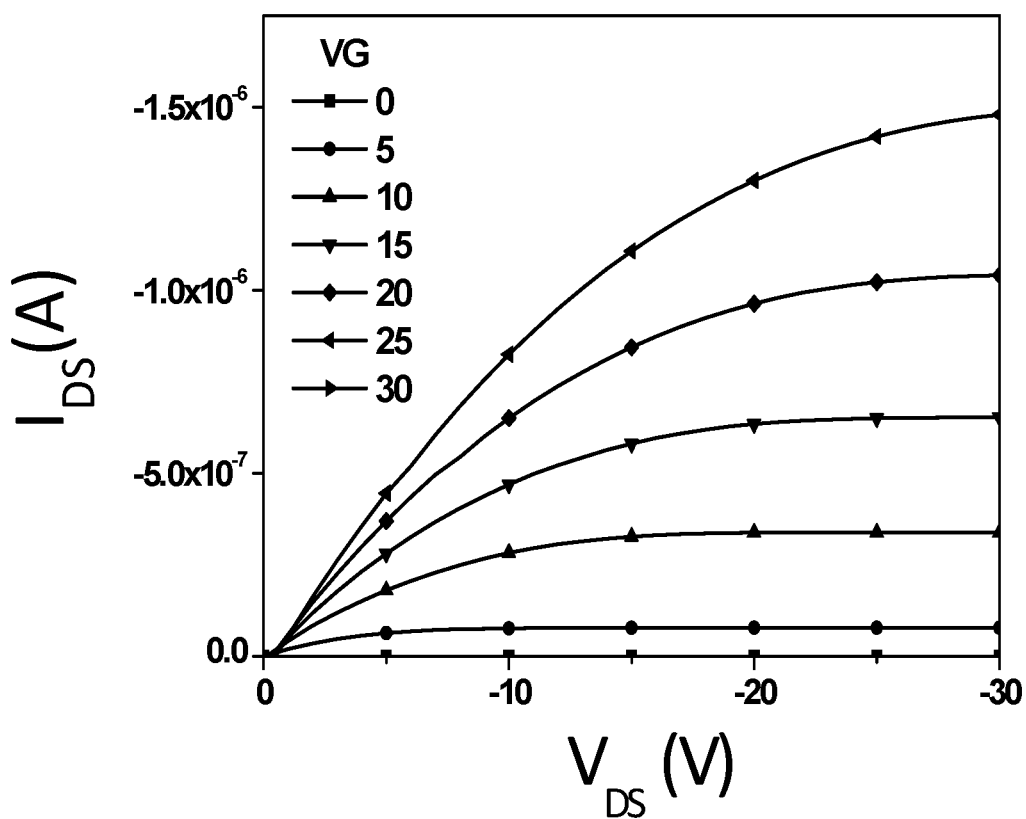
Figure 12:
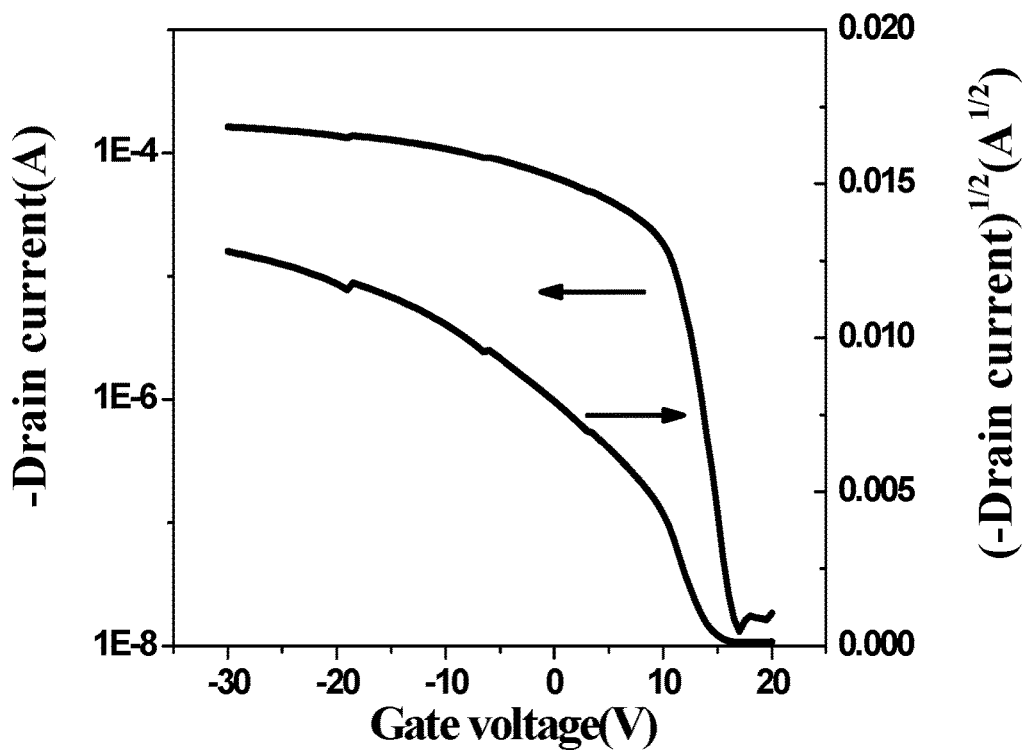
FIGS. 12 and 13 are graphs illustrating properties (transfer curve, output curve) of a device manufactured using a diketopyrrolopyrrole polymer (P-29-DPPDBTE) according to Example 4 by the method of Example 6 after thermal treatment at 200° C.
Figure 13:
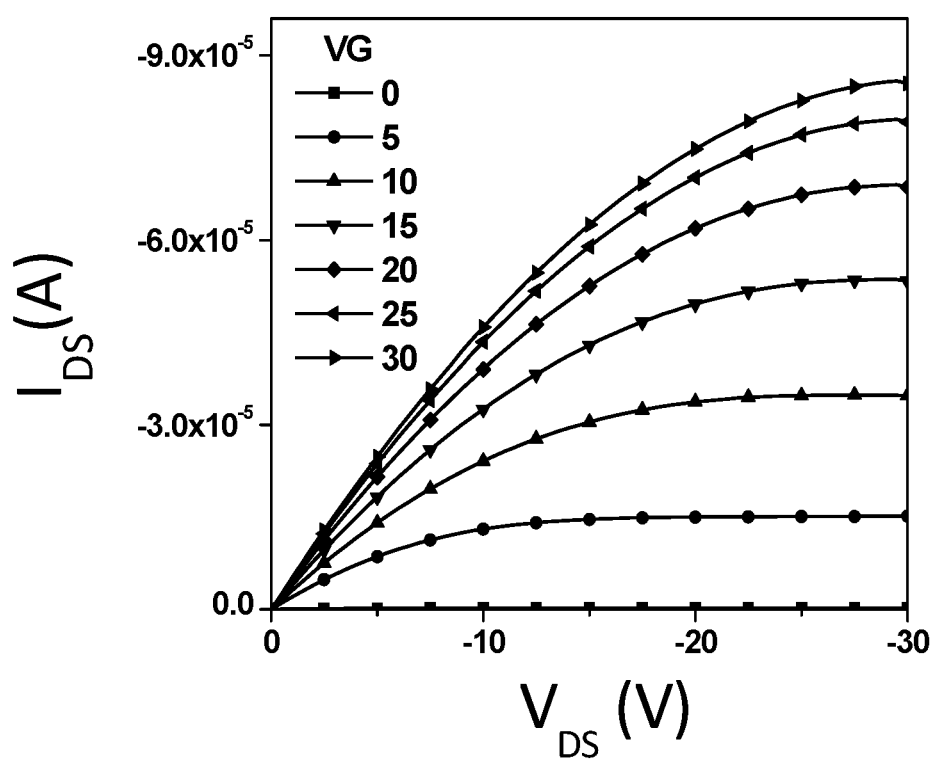

FIGS. 10 and 11, which are graphs illustrating a transfer curve of the device manufactured in Example 6 using the diketopyrrolopyrrole polymer (P-29-DPPDBTE) synthesized in Example 4, are graphs illustrating properties of the organic electronic device of the polymer material, and FIGS. 12 and 13, which are graphs illustrating a transfer curve of the device manufactured in Example 6 using the diketopyrrolopyrrole polymer (P-29-DPPDBTE) synthesized in Example 4 after thermal treatment at 200° C., are graphs illustrating properties of the organic electronic device of the polymer material.

Figure 14:
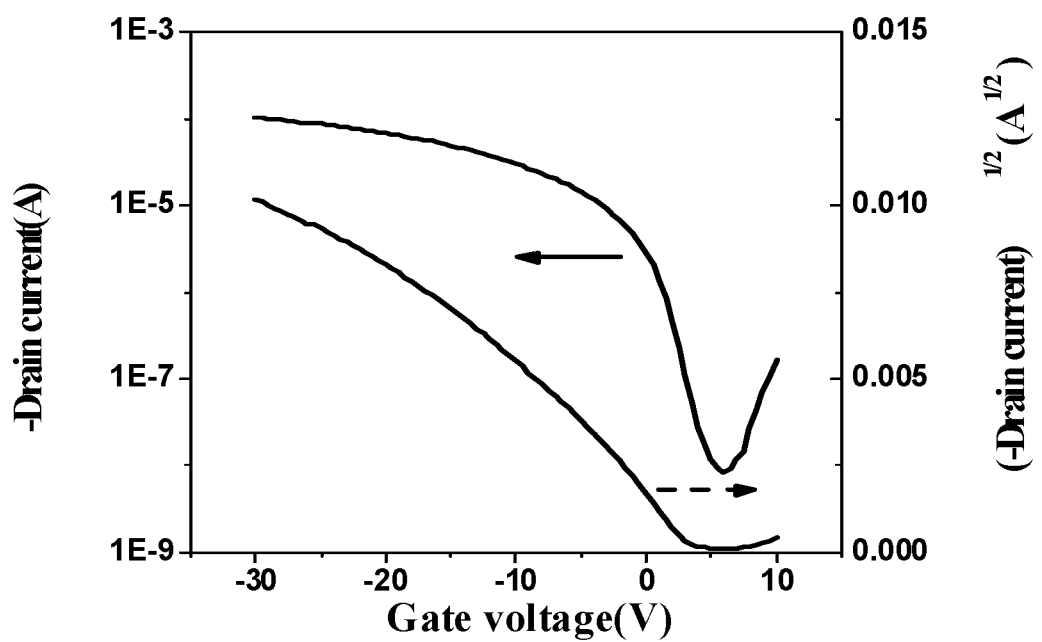
FIGS. 14 and 15 are graphs illustrating properties (transfer curve, output curve) of a device manufactured using a diketopyrrolopyrrole polymer (P-29-DPPDTSE) according to Example 5 by the method of Example 6.
Figure 15:
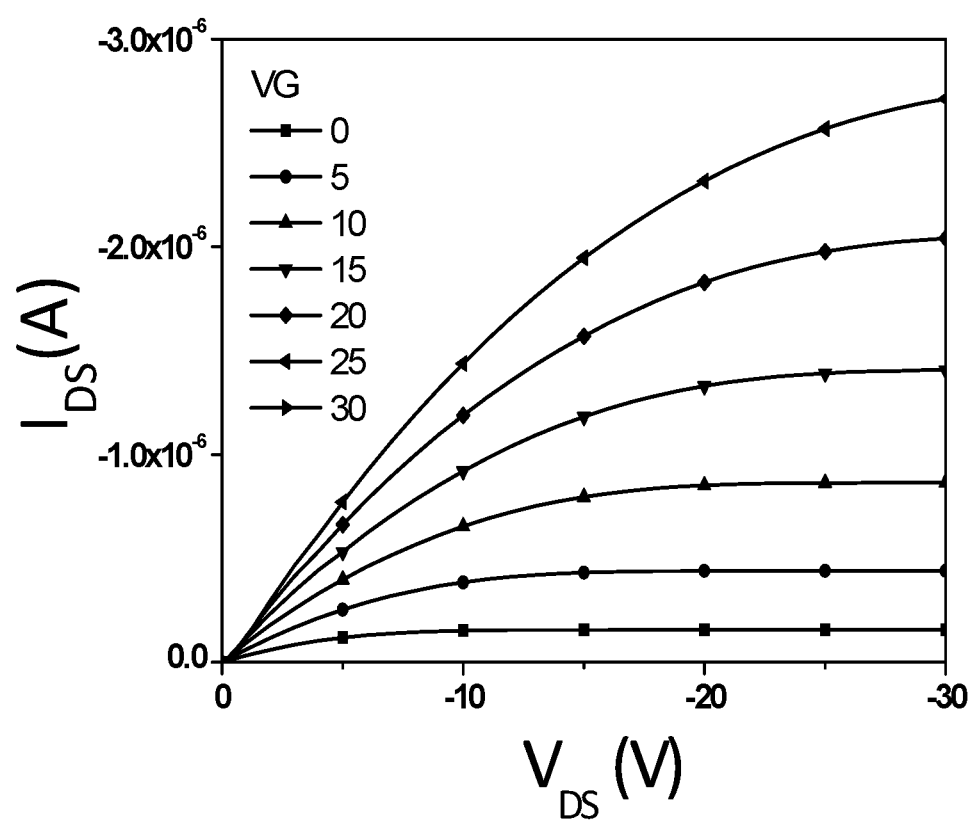
Figure 16:
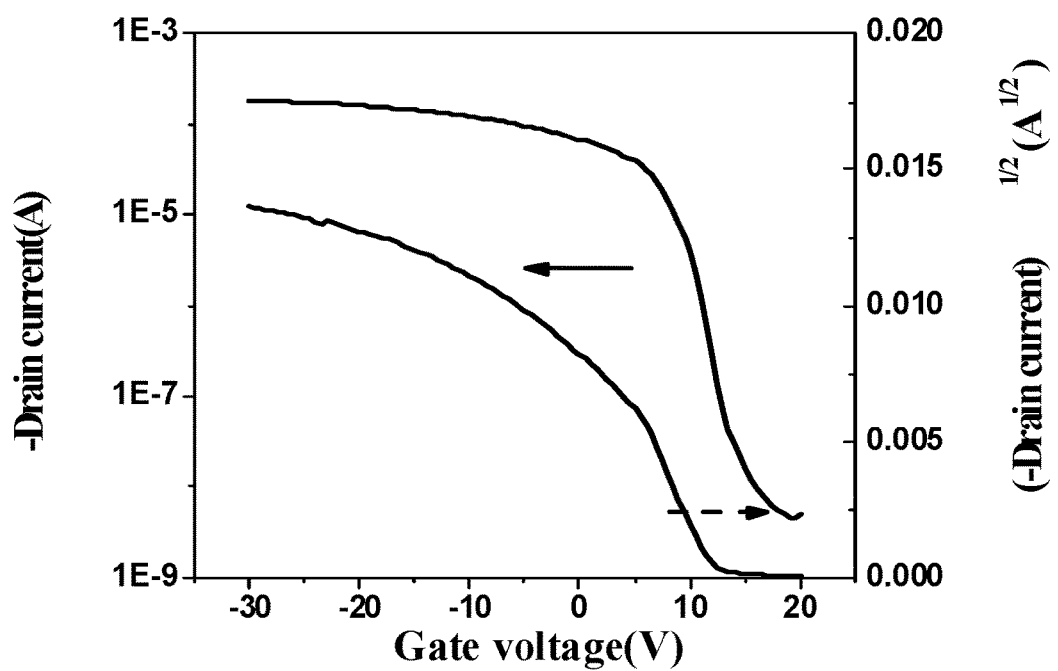
FIGS. 16 and 17 are graphs illustrating properties (transfer curve, output curve) of a device manufactured using a diketopyrrolopyrrole polymer (P-29-DPPDTSE) according to Example 5 by the method of Example 6 after thermal treatment at 200° C.
Figure 17:
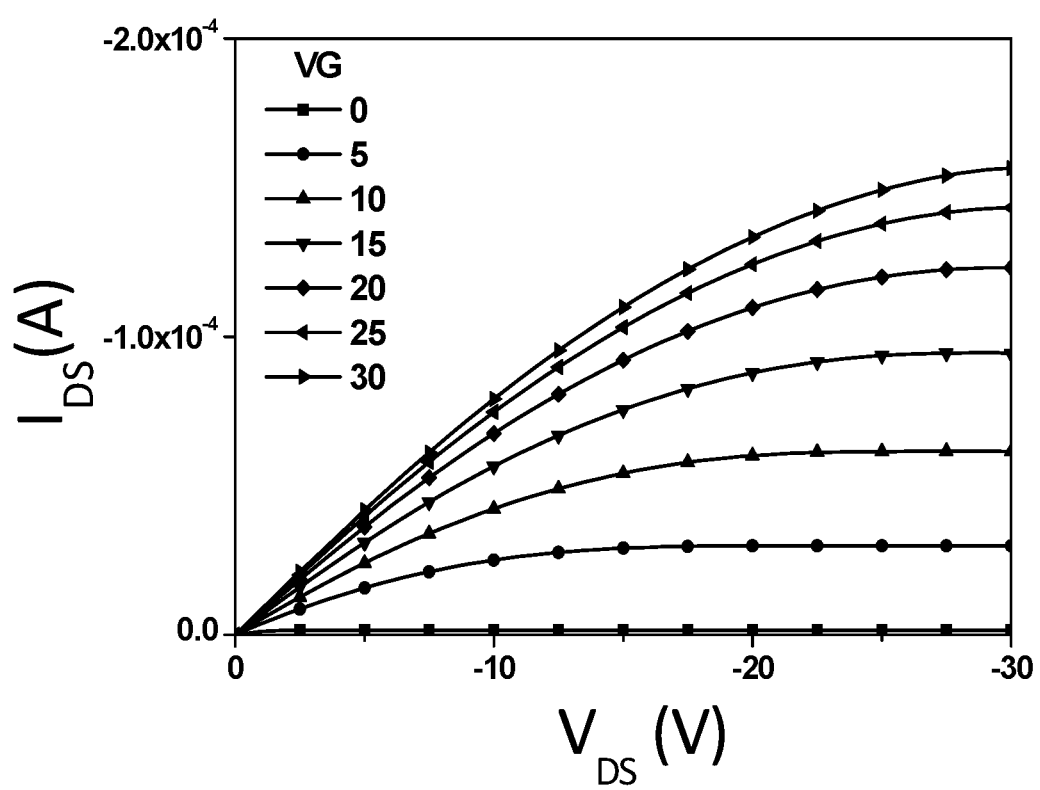

In addition, FIGS. 14 and 15, which are graphs illustrating a transfer curve of the device manufactured in Example 6 using the diketopyrrolopyrrole polymer (P-29-DPPDTSE) synthesized in Example 5, are graphs illustrating properties of the organic electronic device of the polymer material, and FIGS. 16 and 17, which are graphs illustrating a transfer curve of the device manufactured in Example 6 using the diketopyrrolopyrrole polymer (P-29-DPPDTSE) synthesized in Example 5 after thermal treatment at 200° C., are graphs illustrating properties of the organic electronic device of the polymer material.

The properties of the devices manufactured in Example 6 using the diketopyrrolopyrrole polymers (P-29-DPPDBTE and P-29-DPPDTSE) synthesized in Examples 4 and 5 are illustrated in the following Table 2.

TABLE 1

| Polymer | Optical Properties | | | Electrochemical Properties | | |
|---|---|---|---|---|---|---|
| | $UV\lambda_{max}^{sol}$ (nm) | $UV\lambda_{max}^{film}$ (nm) | UV-edge (nm) | Band gap (optical) (eV) | Oxidation onset (eV) | $E_{HOMO}$ (eV) |
| P-29-DPPDBTE (Example 4) | 802 | 812 | 996 | 1.24 | 0.85 | 5.25 |
| P-29-DPPDTSE (Example 5) | 822 | 830 | 998 | 1.23 | 0.87 | 5.27 |

As illustrated in Table 1, the band gap values of the diketopyrrolopyrrole polymers according to the present invention were low, such that charge mobility of the organic electronic devices containing the same was high.

Figure 6:
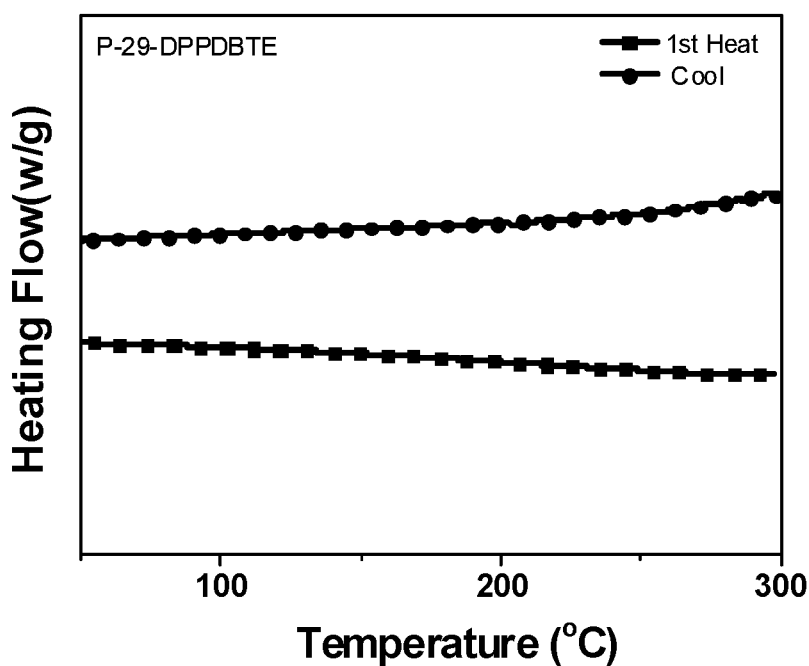
FIG. 6 is a differential scanning calorimetry (DSC) curve of the diketopyrrolopyrrole polymer P-29-DPPDBTE according to Example 4.
Figure 7:
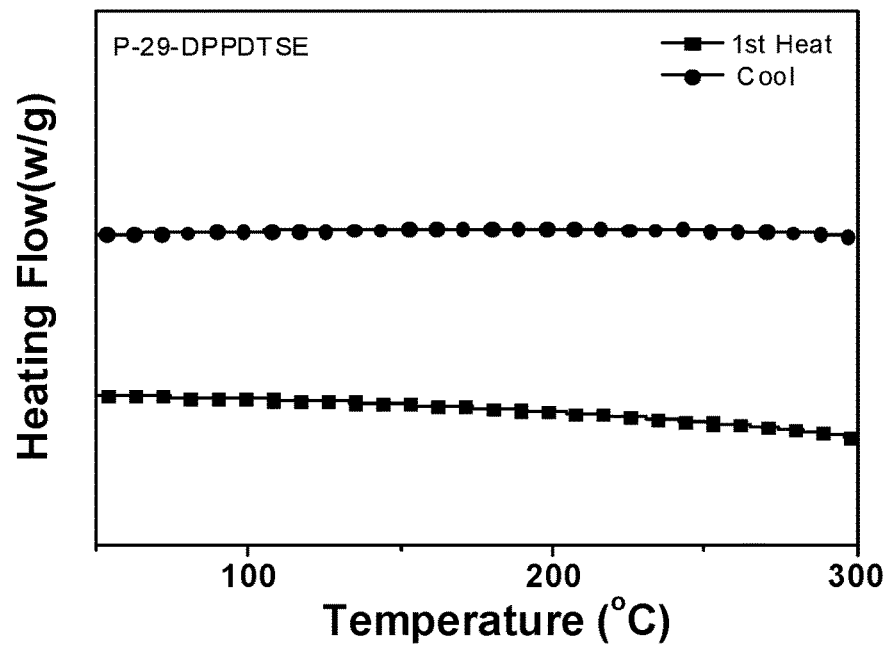
FIG. 7 is a differential scanning calorimetry (DSC) curve of the diketopyrrolopyrrole polymer P-29-DPPDTSE according to Example 5.

FIGS. 6 and 7 illustrate measurement results using DSC in order to measure thermal stability of the diketopyrrolopyrrole polymers (P-29-DPPDBTE and P-29-DPPDTSE) synthesized in Examples 4 and 5.

Figure 8:
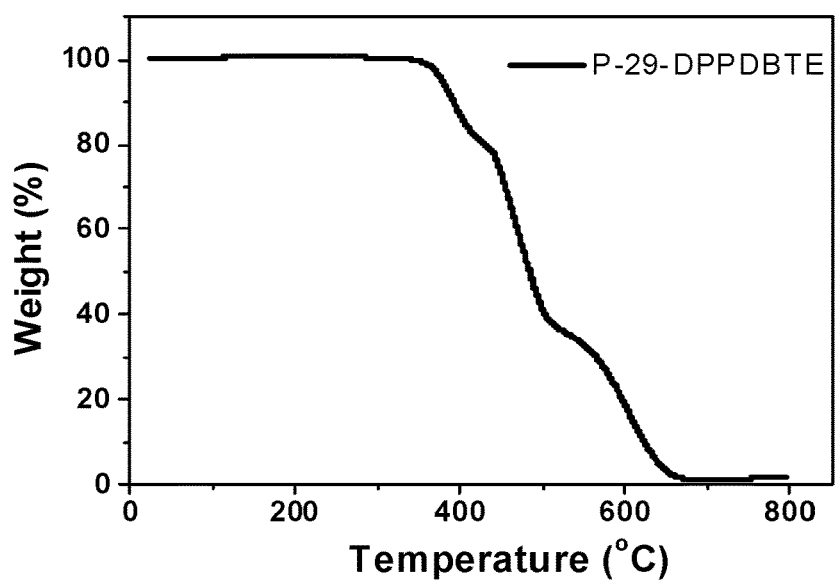
FIG. 8 is a thermogravimetric analysis (TGA) curve of the diketopyrrolopyrrole polymer P-29-DPPDBTE according to Example 4.
Figure 9:
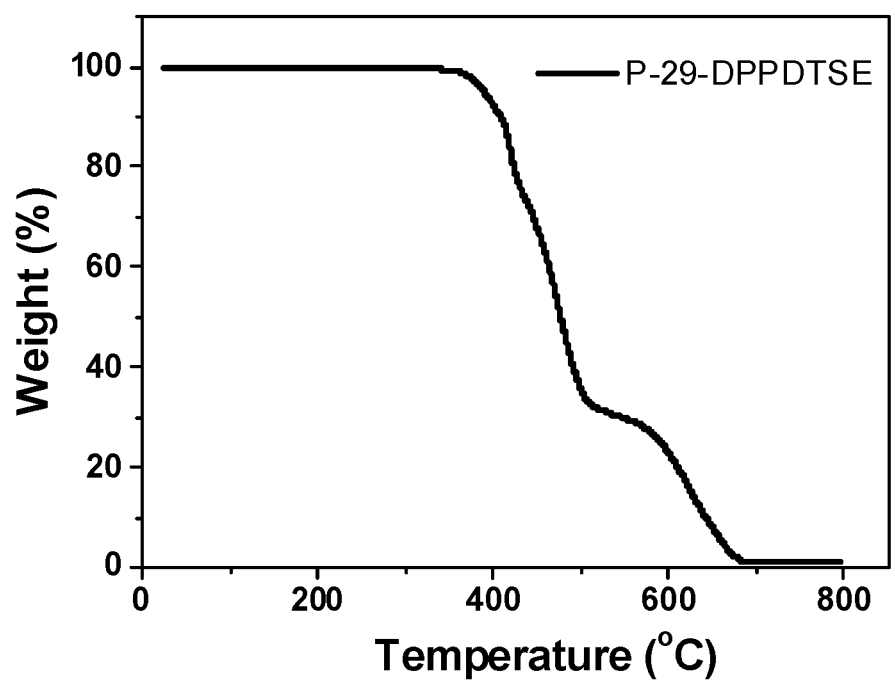
FIG. 9 is a thermogravimetric analysis (TGA) curve of the diketopyrrolopyrrole polymer P-29-DPPDTSE according to Example 5.

FIGS. 8 and 9 illustrate results obtained by measuring decomposition temperatures of the diketopyrrolopyrrole polymers (P-29-DPPDBTE and P-29-DPPDTSE) synthesized in Examples 4 and 5 using TGA.

TABLE 2

| Polymer | Thermal Treatment | Surface Modification | Mobility ($cm^2/(V\,s)$) | Threshold Voltage (V) | On/off Ratio |
|---|---|---|---|---|---|
| P-29-DPPDBTE | Room Temperature | OTS-18 | 0.52 | 9.7 | $7 \times 10^4$ |

TABLE 2-continued

| Polymer | Thermal Treatment | Surface Modification | Mobility ($cm^2/(V\,s)$) | Threshold Voltage (V) | On/off Ratio |
|---|---|---|---|---|---|
| (Example 4) | 180° C. | OTS-18 | 6.32 | 11.4 | $8.3 \times 10^4$ |
| P-29-DPPDTSE | Room Temperature | OTS-18 | 0.6 | 6.5 | $6 \times 10^4$ |
| (Example 5) | 200° C. | OTS-18 | 8.4 | 8.3 | $3.1 \times 10^5$ |

As illustrated in Table 2, the organic electronic devices manufactured by the method in Example 6 and thermally treated at 200° C. contained the diketopyrrolopyrrole polymers according to the present invention, thereby having high charge mobility and stable on/off ratios.

The invention claimed is:

1. A diketopyrrolopyrrole polymer selected from the group consisting of the following structures:

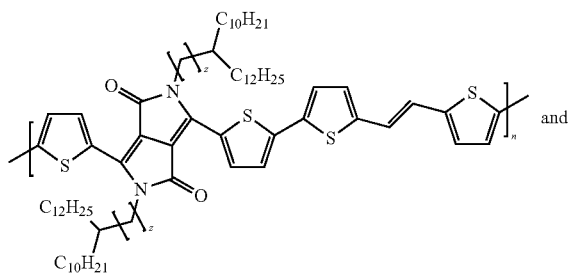

and

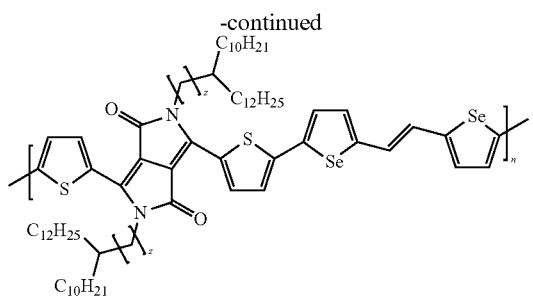

z is an integer of 6 to 8; and n is an integer of 1 to 1,000.

2. An organic electronic device comprising the diketopyrrolopyrrole polymer of claim 1.

* * * * *